United States Defensive Publication [19] (H) [11] T962,009
Fugitt [43] Sept. 6, 1977

[54] REDUCTION OF 2-ACYL-1-NAPHTHOLS TO 2-ALKYL-1-NAPHTHOLS

[76] Inventor: Robert Benson Fugitt, 23 Alwyn Road, Newark, Del. 19713

[21] Appl. No.: 781,105

[22] Filed: Mar. 25, 1977

Related U.S. Application Data

[63] Continuation-in-part of Ser. No. 672,725, April 1, 1976, abandoned.

[51] Int. Cl.[2] ..... C07C 39/14
[52] U.S. Cl. ..... 260/624 C

[57] ABSTRACT

Hydrogenation of 2-acyl-1-naphthols at 200 to 1000 pounds per square inch and 115° to 200° C. in the presence of a copper chromite catalyst produces the corresponding 2-alkyl-1-naphthols. These compounds are useful in the synthesis of 2-alkyl naphthoquinone miticides.

5 Claims, No Sheets Drawing,

9 Pages Specification

The file of this unexamined application may be inspected and copies thereof may be purchased (849 O.G. 1221, Apr. 9, 1968).